(12) United States Patent
Gancet

(10) Patent No.: US 6,337,421 B1
(45) Date of Patent: Jan. 8, 2002

(54) PURIFICATION OF ALKANESULPHONIC ACIDS

(75) Inventor: Christian Gancet, Lons (FR)

(73) Assignee: Atofina, Puteaux (FR)

( * ) Notice: Subject to any disclaimer, the term of this patent is extended or adjusted under 35 U.S.C. 154(b) by 0 days.

(21) Appl. No.: 09/627,002

(22) Filed: Jul. 27, 2000

(30) Foreign Application Priority Data

Jul. 27, 1999 (FR) .............................................. 9909712

(51) Int. Cl.$^7$ .............................................. C07C 309/00
(52) U.S. Cl. ...................................... 562/124; 562/115
(58) Field of Search ........................... 562/124, 30, 115

(56) References Cited

U.S. PATENT DOCUMENTS

| | | | | |
|---|---|---|---|---|
| 2,591,573 A | * | 4/1952 | McBurney | |
| 3,030,411 A | * | 4/1962 | Leum et al. | |
| 3,496,224 A | | 2/1970 | Ayers et al. | |
| 5,028,736 A | | 7/1991 | Gittbach et al. | |
| 5,434,301 A | | 7/1995 | Kozak | |

FOREIGN PATENT DOCUMENTS

| | | |
|---|---|---|
| FR | 2 305 429 | 10/1976 |
| GB | 1 264 293 | 2/1972 |

* cited by examiner

*Primary Examiner*—Jean F. Vollano
(74) *Attorney, Agent, or Firm*—Smith, Gambrell & Russell, LLP

(57) ABSTRACT

In order to reduce the content of sulphuric acid in an alkanesulphonic acid, an aqueous solution of the latter is brought into contact with a basic anion-exchange resin.

The invention relates more particularly to the purification of 70% methanesulphonic acid.

16 Claims, No Drawings

PURIFICATION OF ALKANESULPHONIC ACIDS

FIELD OF THE INVENTION

The present invention relates to the field of sulphonic acids and has more particularly as subject-matter the purification of alkanesulphonic acids, such as methanesulphonic acid (MSA), for the purpose of reducing the content of sulphuric acid therein.

BACKGROUND OF THE INVENTION

Alkanesulphonic acids and more particularly MSA are of use as esterification catalysts and in the plating of conductive metals.

The synthesis of these acids by oxidation of the corresponding thiol, by hydrolysis of an alkanesulphonyl halide or by oxidation of dimethyl disulphide generates various impurities, the presence of which can prove to be a nuisance during use. This is particularly the case for sulphuric acid, which can be found in MSA at concentrations ranging from a few hundred to a few thousand ppm and whose presence is harmful in the use of MSA in the plating of conductive metals; for this application, the commercial specification requires a sulphuric acid content of less than 150 ppm.

In contrast to other impurities, such as hydrochloric acid, sulphuric acid cannot be removed by stripping. Various methods for removing sulphuric acid are known but none of these methods, whether physical (fractional crystallization or separation through a nanofiltration membrane) or chemical (precipitation of alkaline earth metal sulphates, selective electrochemical reduction of $H_2SO_4$ or selective reduction of $H_2SO_4$ by hydrogen sulphide) gives a satisfactory result.

It has now been found that the content of sulphuric acid in an alkanesulphonic acid can be greatly reduced by bringing the latter into contact with a basic anion-exchange resin.

A person skilled in the art knows that basic resins, in particular strong basic resins, are capable of attaching the various anions with a variable affinity which depends on the nature of the anion under consideration and on the potential number of charges capable of being carried by this anion.

DETAILED DESCRIPTION OF THE INVENTION

It is, on the other hand, surprising for a basic anion-exchange resin to be able to selectively attach sulphuric acid present at low concentration in a highly concentrated alkanesulphonic acid (for example MSA). This is because it might have been expected that a high concentration of alkanesulphonic acid would prevent any selectivity from being expressed, all the more so since, in this highly acidic medium, the sulphuric acid is probably not ionized and must therefore be exchanged with the counterion present on the resin under conditions which are a priori not very favourable.

A subject-matter of the invention is therefore a process for the purification of an alkanesulphonic acid in order to reduce the content of sulphuric acid therein and, incidentally, that of anions other than the alkanesulphonate anion, characterized in that it comprises at least one stage in which an aqueous solution of the alkanesulphonic acid to be purified is brought into contact with a basic anion-exchange resin.

Although the process according to the invention is, in the first place, targeted at the purification of MSA, it can also be applied to that of any water-miscible alkanesulphonic acid, in particular acids comprising up to 12 carbon atoms and more particularly those comprising up to 4 carbon atoms, such as ethanesulphonic acid, n-propanesulphonic acid and n-butanesulphonic acid.

The content by weight of alkanesulphonic acid in the aqueous solution of alkanesulphonic acid to be purified can vary within wide limits (10 to 90%, depending on the nature of the acid) but it is advantageously between 60 and 80% and generally in the region of 70% (usual content of commercial MSA. solutions).

The basic anion-exchange resins to be used in the implementation of the process according to the invention are well known and are commercially available. Use may be made of weak basic resins, such as those carrying secondary amine (for example dialkylamino) functional groups, but it is preferable to employ strong basic resins, such as those carrying quaternary ammonium functional groups, in particular —$N^{\oplus}R_3$ groups where R is a $C_1$ to $C_4$ alkyl radical, preferably methyl. These functional groups are generally attached to a polystyrene-divinylbenzene copolymer with a macroporous structure. The preferred anion-exchange resins according to the invention are those sold under the name Diaion® HPA25 by the Company Resindion and under the name Amberlite® IRA92 by the Company Rohm & Haas.

These resins are generally not very stable thermally. For this reason, they must be brought into contact with the aqueous solution of alkanesulphonic acid to be purified at a temperature not exceeding that resulting in decomposition of the resin- The latter is generally below 120° C.; consequently, the process according to the invention is advantageously carried out below 80° C. and preferably at room temperature.

It is preferable to use resins in their chloride form as, after bringing into contact with the alkanesulphonic acid to be purified and separating by any appropriate known means (in particular by filtration, percolation, centrifuging, and the like), the hydrochloric acid formed by the exchange of the sulphate and chloride anions can be easily removed by stripping the purified solution. This operation can be carried out under vacuum and under warm conditions (25 to 120° C., preferably from 30 to 80° C.), optionally with addition of steam. In the case of MSA, it is thus possible to obtain an acid comprising less than 100 ppm of sulphuric acid and less than 10 ppm of hydrochloric acid.

The efficiency of the purification obviously depends on the time during which the aqueous solution of alkanesulphonic acid is brought into contact with the basic resin and on the state of saturation of the latter. The throughput (bv), which is the volume of liquid to be treated with respect to the volume of resin and per hour, can range from 0.1 to 5 but it is advantageous to carry out the purification at a value bv of less than 2.5 and preferably at most equal to 0.5.

DESCRIPTION OF THE PREFERRED EMBODIMENT

In the following examples, which illustrate the invention without limiting it, the percentages and ppm are expressed by weight. The experimental device used was composed of a peristaltic pump, feeding, from a reservoir of MSA to be purified, a glass column comprising 20 ml of anion-exchange resin, and, at the outlet of this column, of a receptacle for the purified MSA.

EXAMPLE 1

Use was made of the Diaion® HPA25 resin in the form of beads with a size of 0.3–0.35 mm (effective size) and with a uniformity coefficient ≦1.5. This strong basic resin of high porosity comprising trimethylammonium groups in the Cl° a form exhibits the following characteristics:

| | |
|---|---|
| backbone | styrene-divinylbenzene copolymer |
| total exchange capacity | ≧0.6 eq/l |
| water retention | 58–68% |
| maximum temperature of use | 100° C. |
| density | 630 g/l |

The MSA solution treated was an MSA-water mixture comprising 70% of MSA and approximately 450 ppm of sulphuric acid.

The tests were carried out at two different throughputs (bv), namely 0.5 and 2.5, corresponding respectively to 10 and 50 ml/h of MSA to be purified.

The results obtained are collated in the following table, which shows the concentration of sulphuric acid as a function of the volume (V in ml) of MSA treated.

| V (ml) | bv = 0.5 [H$_2$SO$_4$] ppm | bv = 2.5 [H$_2$SO$_4$] ppm |
|---|---|---|
| 10 | 20 | 19.5 |
| 20 | 22 | 29 |
| 30 | 25 | 51.2 |
| 40 | 35 | 86 |
| 50 | 71 | 131.7 |

EXAMPLE 2

Example 1 was repeated at a throughput (bv) using a 70% MSA solution comprising approximately 1900 ppm of sulphuric acid.

The results obtained are collated in the following table.

| V (ml) | 5 | 10 | 32 | 42 | 52 |
|---|---|---|---|---|---|
| [H$_2$SO$_4$] ppm | <5 | 33 | 45 | 130 | 434 |

EXAMPLE 3

Example 1 was repeated at a throughput (bv) of 2.5, the Diaion® HPA25 resin being replaced with Amberlite® IRA92 resin. This weakly basic resin comprising dialkylamino groups exhibits the following characteristics:

| | |
|---|---|
| backbone | macroporous polystyrene |
| total exchange capacity | ≧1.6 eq/l |
| water retention | 40–50% |
| maximum temperature of use | 90° C. |
| density | 620–690 g/l |
| physical appearance | beads with an effective size ≧450 μm and a uniformity coefficient ≦1.8 |

The results are collated in the following table:

| V (ml) | 10 | 20 | 40 |
|---|---|---|---|
| [H$_2$SO$_4$] ppm | 18 | 65 | 151 |

Although the invention has been described in conjunction with specific embodiments, it is evident that many alternatives and variations will be apparent to those skilled in the art in light of the foregoing description. Accordingly, the invention is intended to embrace all of the alternatives and variations that fall within the spirit and scope of the appended claims. The above references are hereby incorporated by reference.

What is claimed is:

1. Process for the purification of an alkanesulphonic acid to reduce the content of sulphuric acid therein and, of anions other than the alkanesulphonate anion, comprising at least one stage in which an aqueous solution of the alkanesulphonic acid to be purified is brought into contact with a basic anion-exchange resin.

2. Process according to claim 1, wherein the aqueous solution comprises between 60% and 80% by weight of the alkanesulphonic acid.

3. Process according to claim 1, wherein the basic anion-exchange resin with which the aqueous solution is contacted is the chloride form of a quaternary amine resin.

4. Process according to claim 1, wherein contacting is carried out at a temperature not exceeding that resulting in decomposition of the resin.

5. Process according to claim 1, wherein the solution is contacted with said resin at an hourly throughput of between 0.1 and 5 parts by volume of said solution per 1 part by volume of the resin.

6. Process according to claim 1, wherein after contacting, the resulting product is subjected to a stripping stage.

7. Process according to claim 6, wherein the stripping is carried out under vacuum and at a temperature ranging from 25 to 120° C.

8. Process according to claim 1, wherein the alkanesulphonic acid to be purified comprises an alkyl group containing from 1 to 12 carbon atoms.

9. Process according to claim 1, wherein the alkanesulphonic acid is methanesulphonic acid in an aqueous solution comprising 70% by weight of the methanesulphonic acid.

10. Process according to claim 2, wherein the aqueous solution comprises about 70% by weight of the alkanesulphonic acid.

11. Process according to claim 4, wherein the temperature is less than 80° C.

12. Process according to claim 11, wherein the temperature is room temperature.

13. Process according to claim 5, wherein the solution is contacted with said resin at an hourly throughput of less than 2.5 parts by volume of said solution per 1 part by volume of the resin.

14. Process according to claim 13, wherein the solution is contacted with said resin at an hourly throughput of at most 0.5 parts by volume of said solution per 1 part by volume of the resin.

15. Process according to claim 7, wherein the temperature ranges from 30 to 80° C.

16. Process according to claim 8, wherein the acid is methanesulphonic acid.

* * * * *